United States Patent
Plumley et al.

(10) Patent No.: US 9,655,553 B2
(45) Date of Patent: *May 23, 2017

(54) COMPACT BIOSENSOR OF MATRIX METALLOPROTEINASE WITH CADMIUM FREE QUANTUM DOTS

(71) Applicant: STC.UNM, Albuquerque, NM (US)

(72) Inventors: John B. Plumley, Albuquerque, NM (US); Erin D. Milligan, Placitas, NM (US); Marek Osinski, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/850,221

(22) Filed: Sep. 10, 2015

(65) Prior Publication Data

US 2016/0029930 A1 Feb. 4, 2016

Related U.S. Application Data

(63) Continuation of application No. 13/487,933, filed on Jun. 4, 2012, now Pat. No. 9,155,497.

(60) Provisional application No. 61/492,680, filed on Jun. 2, 2011.

(51) Int. Cl.
| | |
|---|---|
| *A61B 5/1455* | (2006.01) |
| *G01N 33/58* | (2006.01) |
| *A61B 5/1459* | (2006.01) |
| *A61B 5/00* | (2006.01) |
| *A61B 5/1473* | (2006.01) |

(52) U.S. Cl.
CPC .......... *A61B 5/1455* (2013.01); *A61B 5/1459* (2013.01); *A61B 5/14735* (2013.01); *A61B 5/4058* (2013.01); *A61B 5/6852* (2013.01); *A61B 5/6877* (2013.01); *G01N 33/588* (2013.01); *A61B 2562/0233* (2013.01); *A61B 2562/0285* (2013.01)

(58) Field of Classification Search
CPC ........................... A61B 5/1459; A61B 5/1455
See application file for complete search history.

(56) References Cited

U.S. PATENT DOCUMENTS

| | | | |
|---|---|---|---|
| 7,229,769 B2 | 6/2007 | Kozlov et al. | |
| 9,155,497 B1 | 10/2015 | Plumley et al. | |
| 2009/0068108 A1 | 3/2009 | Sokolov et al. | |
| 2013/0112942 A1 | 5/2013 | Kurtin et al. | |

OTHER PUBLICATIONS

Sambrook, et al. 1989, Molecular Cloning, Second Edition. Cold Spring Harbor Laboratory Press, Plainview, New York.
Maniatis, et al. 1982, Molecular Cloning. Cold Spring Harbor Laboratory, Plainview, New York.
Wu (Ed.) 1993, Meth Enzymol. 218, Part 1. Academic Press, New York.
Wu (Ed.) 1979, Meth Enzymol. 68. Academic Press, New York.

(Continued)

*Primary Examiner* — Eric Winakur
(74) *Attorney, Agent, or Firm* — Henry D. Coleman; R. Neil Sudol

(57) ABSTRACT

The invention provides a quantum dot (QD) modified optical fiber-based biosensor which characterizes matrix metalloproteinase (MMP) enzyme activity at pain signaling sites in the central nervous system (CNS) in vivo. Related systems and peptide biomarker screening methods are also provided.

10 Claims, 9 Drawing Sheets

(56) References Cited

OTHER PUBLICATIONS

Wu, et al. (Eds.) 1983, Meth Enzymol. vol. 100 and 101; Academic Press, New York.
Grossman and Moldave. (Eds.) 1980 Meth Enzymol. 65; Academic Press, New York.
Miller. (Ed.) 1972, Experiments in Molecular Genetics. Cole Spring Harbor Laboratory, Cold Spring Harbor, New York.
Old, Primrose. 1981, Principles of Gene Manipulation. University of California Press, Berkely.
Scheif, Wensink. 1982, Practical Methods in Molecular Biology. Springer-Verlag, New York.
Glover. (Ed.) 1985, DNA Cloning vol. I and II. IRL Press, Oxford, UK.
Hames, Higgins. (Eds.) 1985, Nucleic Acid Hybridization. IRL Press, Oxford, UK.
Setlow, Hollaender. 1979, Genetic Engineering Principles and Methods, vol. 1-4. Plenum Press, New York.
Setubal, Meidanis. 1997, Introduction to Computational Molecular Biology. PWS Publishing Company, Boston.
Salzberg, Searles, Kasif. (Ed.) 1998, Computational Methods in Molecular Biology. Elsevier, Amsterdam.
Rashidi, Buehler. 2000, Bioinfomatics Basics: Applications in Biological Science and Medicine.
Baxevanis, Ouellette. 2001, Bioinformatics: A Practical Guide for Analysis of Gene and Proteins. 2.sup.nd. ed; Wiley & Sons, Inc. New York.
Xu X, et al. Functional basis for the overlap in ligand interactions and substrate specificities of matrix metalloproteinases-9 and -2 (MMP-9 and -2). Biochemical Journal Immediate Publication, 2005; http://www.biochemj.org/bj/imps_x/pdf/BJ20050650.pdf.
Acharya S, et al. An Alternate Route to High-Quality ZnSe and Cu—Doped ZnSe Nanocrystals. J Phys Chem Lett, 2010;1:485-488.
Adair J, et al. Measurement of gelatinase B in the cerebrospinal fluid of patients with vascular dementia and Alzheimer disease. Stroke, 2004;35:e159-e162.
Dev R, et al. Therapeutic potential of matrix metalloprotease inhibitors in neuropathic pain. Expert Opinion on Investigational Drugs, 2010;19(4):455-468.
Hu M, et al. Structure and morphology of self-assembled 3-mercaptopropyltrimethoxysilane layers on silicon oxide. Applied Surface Science, 2001;181:307-316.
Leppert D, et al. Matrix metalloproteinase-9 is selectively elevated in CSF during relapses and stable phases of multiple sclerosis. Brain, 1999;121:2327-2334.
Li C, et al. Highly luminescent water-soluble InP/ZnS nanocrystals prepared via reactive phase transfer and photochemical processing. J Phys Chem C, 2008;112:20190-20199.
Liuzzi Gm, et al. Increased activity of matrix metalloproteinases in the cerebrospinal fluid of patients with HIV-associated neurological diseases. Journal of Neurovirology, 2000;6:156-163.
Melville P, et al. Proteinase and Phospholipase activities and development at different temperatures of yeasts isolated from bovine milk. Journal of Dairy Research, 2011;78:385-390.
Niebroj-Dobosz I, et al. Matrix metalloproteinases and their tissue inhibitors in serum and cerebrospinal fluid of patients with amyotrophic lateral sclerosis. European Journal of Neurology, 2010;17:226-231.
Pradhan N, et al. An Alternative of CdSeNanocrystal Emitters: Pure and Tunable Impurity Emissions in ZnSeNanocrystals. J Am Chem Soc, 2005;127(5):17586-17587.
Turk B, et al. Determination of protease cleavage site motifs using mixture-based oriented peptide libraries. Nature Biotechnology, 2001;19:661-667.
Wagner K. The need for biomarkers in amyotrophic lateral sclerosis development. Neurology, 2009;72:11-12.
Xie Rg, Peng Xg. Synthesis of Cu—doped InP Nanocrystals (d-dots) with ZnSe Diffusion Barrier as Efficient and Color-Tunable NIR emitters. J Am Chem Soc, 2009;131:30:10645-10651.

COMPACT BIOSENSOR OF MATRIX METALLOPROTEINASE WITH CADMIUM FREE QUANTUM DOTS

RELATED APPLICATIONS

This application is a continuation application of U.S. patent application Ser. No. 13/487,933 filed Jun. 4, 2012 which claims priority from U.S. Provisional Application Ser. No. 61/492,680 filed Jun. 2, 2011, entitled "AMYOTROPHIC LATERAL SCLEROSIS DETECTION DEVICES, METHODS, AND BIOMARKERS", the complete disclosure of which said two applications is hereby incorporated by reference in its entirety.

GOVERNMENT SUPPORT

The invention described herein was made with government support under grant number DGE0549500 awarded by the National Science Foundation (NSF). Accordingly, the United States has certain rights in the invention.

FIELD OF THE INVENTION

The invention provides a quantum dot (QD) modified optical fiber-based biosensor which characterizes matrix metalloproteinase (MMP) enzyme activity at pain signaling sites in the central nervous system (CNS) in vivo. Related systems and peptide biomarker screening methods are also provided.

BACKGROUND OF THE INVENTION

Given that existing pain treatments (which primarily target neurons) reduce pain by only around 25-40% in less than half of the 15 million patients suffering from chronic neuropathic pain in the US, there is a need for new methods to identify and investigate pain-related cellular processes beyond only neuronal function.

Of the pain drugs currently available, opioid analgesics are the gold standard despite their addiction liabilities. A biomarker for neuropathic pain does not exist despite the need to objectively identify those individuals in need of treatment.

Further, the neuron centered view of pain processing is changing, and non-neuronal targets are emerging, including glial cells and leukocytes that enrich the spinal cord and other central nervous system sites (CNS) critical for pathological pain signaling. Thus, it is possible that by targeting non-neuronal signaling mechanisms, a novel biomarker to identify neuropathic pain may emerge.

Indeed, upon strong pain-related neuronal activation, spinal cord glia contribute to persistent pathological pain by responding to and releasing proinflammatory cytokines like IL-1β & TNF-α as well as the activity of matrix metalloproteinase (MMP) enzymes [Dev 2010]. Leukocytes may additionally contribute to ongoing pathological pain by releasing and responding to IL-1β and TNF-α, with an additional contribution of MMPs. However, MMPs not only contribute to the neuroinflammation, but may be directly involved in pain-associated nerve damage.

There has been an increasing interest in matrix metalloproteinase (MMP) enzyme biosensing activity as a biomarker for neurological diseases. Several studies on MMP activity in patients with neurological diseases generally indicate abnormal MMP activity in the serum and CSF. In specific, patients with amyotrophic lateral sclerosis (ALS) statistically show 3 times lower MMP-9 activity in the CSF and 2 times higher MMP-9 activity in the serum, in comparison to healthy controls [Niebroj-Dobosz 2010]. Furthermore, it was statistically shown that patients with HIV [Liuzzi 2000] and multiple sclerosis [Leppert 1998] have increased MMP-9 activity, while patients with Alzheimer's show no abnormal MMP-9 activity at all [Adair 2004]. Most of these findings were done via gel electrophoresis; a multistep assay process. A simpler and highly effective sensing method for indicating these findings could have a positive impact on clinical treatment.

MMPs are zinc dependent endopeptidases which can bind to specific non-terminal amino acids in peptides with specific amino acid sequences. Active MMPs form bonds to amino acid residues at the active site of the MMP, which consists of a highly reactive zinc ion. After binding to a peptide, MMPs will catalyze hydrolysis and break a bond between two amino acid residues in a peptide. MMPs are initially synthesized as inactive by the body's immune system, but become active due to injury, inflammation, or the presence of other proteinases, foreign bodies, and pathogens. Specifically, MMPS are made active by the removal of a peptide blocking the active region due to a bond between the $Zn^{2+}$ ion and the thiol group in the cysteine amino acid residue.

The previous findings reported in literature relating neurological diseases to MMPs are a good indication of their potential as a biomarker. However, in vivo biosensing of MMP activity remains largely unexplored.

SUMMARY OF THE INVENTION

In one embodiment, the invention provides a quantum dot (QD) modified optical fiber-based biosensor system adapted for evaluation of metalloproteinase (MMP) enzyme activity at pain signaling sites in the central nervous system (CNS), the system comprising:
(a) a multimode silica optical fiber comprising one or more quantum dots that (1) are bioconjugated on their surface to one or more peptides having an affinity for the metalloproteinase (MMP) enzyme, and (2) that are tethered to an insertion end of said multimode silica optical fiber by one or more silane coupling agents; and
(b) a photon detector;
wherein changes in photon emission resulting from interaction of the metalloproteinase (MMP) enzyme and peptides having an affinity for the metalloproteinase (MMP) enzyme are detected by the photon detector.

In a preferred embodiment, the metalloproteinase (MMP) enzyme activity detected by the system described above is implicated in neuroimmune neuropathies. In certain embodiments, neuroimmune neuropathies include amyotrophic lateral sclerosis (ALS) and multiple sclerosis.

In another embodiment, the insertion end of the multimode silica optical fiber is adapted for insertion into an in-dwelling spinal catheter that is submerged into either the epidermal or intrathecal regions of the central nervous system.

Preferably, in systems and methods of the invention:
(1) the quantum dots do not contain cadmium;
(2) changes in photon emission resulting from interaction of said metalloproteinase (MMP) enzyme and peptides having an affinity for said metalloproteinase (MMP) enzyme are reflected by measurable perturbations in quantum dot fluorescence and are detected by a transducer of said photon detector;

(3) the silane coupling agents comprise a thiol functional group that covalently bonds to metallic surface; and
(4) quantum dots are either colloidal Mn-doped ZnSe/ZnS quantum dots, Cu-doped ZnSe quantum dots or InP/ZnSe quantum dots.

In one embodiment of the systems and methods of the invention:
(a) the one or more peptides having an affinity for the metalloproteinase (MMP) enzyme are modified at either their N or C-terminals with a fluorescent protein or dye;
(b) in operation, the fluorescent protein or dye undergoes Förster resonant energy transfer (FRET) with the quantum dots, the Förster resonant energy transfer (FRET) being disrupted by interaction of said metalloproteinase (MMP) enzyme and peptides having an affinity for the metalloproteinase (MMP) enzyme; and
(c) the disruption is (1) detected by said photon detector, and (2) correlated as an indicator of metalloproteinase (MMP) enzyme activity.

In a preferred embodiment, the photon detector is adapted for the detection of ratiometric changes that occur as quantum dot fluorescence increases and protein fluorescence decreases due to metalloproteinase (MMP) enzyme activity, and in operation the detected ratiometric changes are correlated as an indicator of metalloproteinase (MMP) enzyme activity in vivo.

In another embodiment, the invention provides a method for evaluating in vivo metalloproteinase (MMP) enzyme activity at a subject's central nervous system pain signaling site, the method comprising:
(a) providing a quantum dot (QD) modified optical fiber-based biosensor system as described herein;
(b) inserting the multimode silica optical fiber of the biosensor system into an in-dwelling spinal catheter that is submerged into either the epidermal or intrathecal regions of the subject's central nervous system; and
(c) measuring changes in photon emission resulting from interaction of said metalloproteinase (MMP) enzyme and peptides having an affinity for said metalloproteinase (MMP) enzyme, said changes having been detected by said photon detector.

Förster resonant energy transfer (FRET) disruption techniques as described herein can also be used in the diagnostic methods of the invention. Detection of ratiometric changes that occur as quantum dot fluorescence increases and protein fluorescence decreases due to metalloproteinase (MMP) enzyme activity as described herein provide another aspect of the disclosed diagnostic methods.

In still another embodiment, the invention provides a method for identifying a peptide having an affinity for a metalloproteinase (MMP) enzyme implicated in a neuroimmune neuropathy, the method comprising:
(a) providing a quantum dot (QD) modified optical fiber-based biosensor system of as described herein;
(b) inserting the multimode silica optical fiber of the biosensor system into an in-dwelling spinal catheter that is submerged into either the epidermal or intrathecal regions of a subject's central nervous system; and
(c) measuring any changes in photon emission that result from interaction of said metalloproteinase (MMP) enzyme and said peptide, as detected by said photon detector; and
(d) comparing any changes in photon emission to a control value.

These and other embodiments of the invention are described further in the Detailed Description of the Invention.

DETAILED DESCRIPTION OF THE INVENTION

Figure 1:
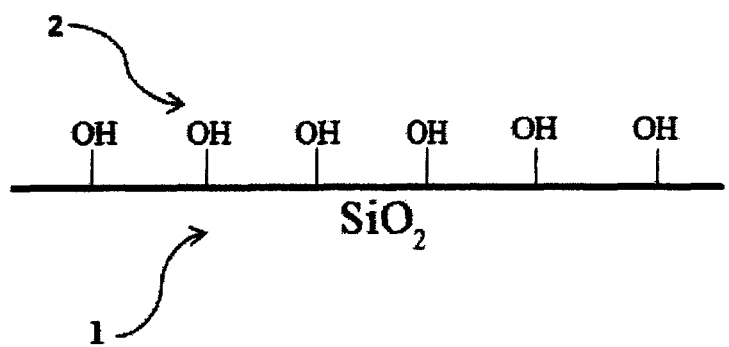
FIG. 1 is an illustration depicting hydroxyl modified silica.

It is noted that, as used in this specification and the appended claims, the singular forms "a," "an," and "the," include plural referents unless expressly and unequivocally limited to one referent. Thus, for example, reference to "a compound" includes two or more different compound. As used herein, the term "include" and its grammatical variants are intended to be non-limiting, such that recitation of items in a list is not to the exclusion of other like items that can be substituted or other items that can be added to the listed items.

As described in U.S. Pat. No. 8,170,665, "quantum dots (QDs) are semiconductor nanoparticles that were discovered in the early 1980's. Certain known QDs used for biological applications consist of a cadmium selenide or cadmium tellurium semiconductor core, a zinc sulfide inner shell and an outer polymer coating. The result is a water-soluble particle 13-15 nm in diameter.

Similar to organic fluorophores, QDs absorb photons of light of one wavelength and emit light of a different wavelength. Traditional fluorophores use absorbed energy to transfer electrons to excited states and energy is released in the form of fluorescent light when these electrons return to their resting states. When electrons move to different energy levels in QDs, they behave analogously, generating electron holes called excitons. The quantum system of excitons makes QD fluorescence much brighter and more photostable (less prone to photobleaching) than traditional fluorophores.

The energy state of an exciton dictates the wavelength of light emitted by a particular QD after excitation. QDs have a unique property known as tunability, wherein the physical size of the QD determines the wavelength of emitted light. Smaller dots emit blue fluorescent light and as the core size of the dots increases, emitted light becomes redder. Another important feature that distinguishes QDs from conventional fluorescent dyes is the large distance between the wavelength of excitation and emission light. This energy difference, known as the Stokes' shift, means that QDs can be excited by ultraviolet light at a wavelength much lower than the peak emission wavelength. Thus, QDs can be excited by any wavelength lower than its emission wavelength. Therefore, particles are excited and emitted light is collected in a very efficient manner."

Preferred quantum dots used in the instant invention include but are not limited to Mn-doped ZnSe/ZnS quantum dots, Cu-doped ZnSe quantum dots InP/ZnSe quantum dots and colloidal Mn-doped ZnSe/ZnS quantum dots. These quantum dots ideally emit light at a wavelength of between about 498 nm to about 750 nm.

Bioconjugated QD probes, which are linked to biological molecules like monoclonal antibodies, peptides, proteins, or nucleic acids and contain bright and stable fluorescent light emission and multiplexing potential (i.e., capability to detect multiple disease markers simultaneously), provide a novel highly sensitive approach to detect low-abundant copy numbers of potential disease biomarkers (e.g., nucleic acids and proteins) in bodily fluid and tissue samples. QDs with their intrinsic high spatial resolution and sensitivity of fluorescence imaging can not only serve as sensitive probes for disease biomarkers, but they could also enable the detection of hundreds to thousands of simultaneously (i.e. multiplexing). See U.S. Patent Application Document No. 20070157325. Those of ordinary skill in the art know how to bioconjugate peptides having an affinity for said metalloproteinase (MMP) enzyme to a quantum dot.

A "multimode silica optical fiber" can include a wide-variety of silica optical fibers known as being useful in vivo diagnostic applications, e.g. around 100 to around 400 µm core diameter (as far as I understand, larger core diameters are needed in order to transmit visible light through silica multi-mode fibers, which are typically 50 µm and designed for ~850-1350 nm light, where I would need visible light according to the characteristics of the QDs presented in this patent) fused silica optical fibers.

"Silane coupling agents" include but are not limited to tetraethoxysilane (TEOS), γ-mercaptopropyltrimethoxysilane (MPS), γ-mercaptopropyltriethoxysilane, γ-aminopropyltriethoxysilane (APS), 3-thiocyanatopropyltriethoxysilane, 3-glycidyloxypropyltriethoxysilane, 3-isocyanatopropyltriethoxysilane, and 3-[2-(2-aminoethylamino)ethylamino]propyl-triethoxysilane.

The order of magnitude of the affinity between a peptide and metalloproteinase (MMP) enzyme can vary between approximately $10^{-10}$ M to around $10^{-5}$ M, and preferentially is between approximately 0.1 nM and approximately 100 nM. The term approximately is used to cover the variability in the measurement of the affinity, with variation typically being from around 5% to 10% measurement error.

"Photon detectors include but are not limited to photodetectors, light detectors, photon counters. In a non-limiting example, photon detectors can comprises at least one three-dimensional (3D) photonic crystal that operates at a relatively low temperature and is formed or grown on a glass substrate, and at least one field emission transistor (FET), e.g., a thin-film transistor (TFT), that is also formed on a glass substrate (e.g., a TFT can have a thin film of silicon, and the transistors are fabricated using this thin layer). In at least one further exemplary embodiment, suitable types of transistors other than FETs can be employed. In at least one exemplary embodiment, the PDC is also referred to as a detection layer. In at least one exemplary embodiment, the photon detector is a digital photon detector. In at least one other exemplary embodiment of the invention, glass is the substrate, although any other compatible substrates providing the optical properties necessary for the present invention (e.g., transparent plastics) are also contemplated.

Scintillation crystals coupled to avalanche photo diodes can also be used as photon detectors. In other embodiments, scintillation crystals are coupled with photomultiplier tubes. The scintillation crystals are bismuth germanium oxide, gadolinium oxyorthosilicate, or lutetium oxyorthosilicate crystals, but other crystals may be used.

Photon detectors can be arranged individually or in groups. The detectors can generate analog signals, position signals or energy signals. Each of the signals can output as a differential signal pair.

Neuroimmune activation have been shown to play a role in the etiology of a variety of neurological disorders such as stroke, Parkinson's and Alzheimer's disease, multiple sclerosis, pain, and AIDS-associated dementia. However, cytokines and chemokines also modulate CNS function in the absence of overt immunological, physiological, or psychological challenges. Essentially any cytokines and cytokine receptor-related disorder is susceptible to diagnosis and screening using the systems and methods of the invention. Chronic pain is an extremely debilitating disease syndrome for which current treatment modalities are largely ineffective. Neuroimmune activation in the maintenance of chronic pain is another process that may be analyzed using the systems and methods of the invention. Further, disorders implicating a pathway that links peripheral neuronal injury/inflammation with the activation of central nervous system neuroglial cells, which contributes to sustained neuronal hyper-excitability, are also subject to assessment by the systems and methods described herein. Preferred systems and methods diagnose and screen for peptide markers for amyotrophic lateral sclerosis (ALS) and multiple sclerosis.

The MMP family of zinc endopeptidases (24 individual enzymes in humans) includes collagenases, gelatinases, matrilysins, stromelysins and membrane-type MMPs. MMP proteolysis regulates the levels and the functionality of extracellular matrix components and cell surface signaling receptors. In the damaged nerves, MMP proteolysis can be both detrimental and beneficial to axonal growth and recovery of neuronal function. In peripheral adult nerves, MMP-9 (gelatinase B) is produced only after injury. After a lesion, MMP-9 is produced by myelinating SCs (mSCs), immune and endothelial cells to promote the breakdown of the myelin sheath, the blood-nerve barrier and the SC basal lamina. MMP-9 is a multi-domain enzyme with wideranging substrate preferences. Earlier work suggests that MMP-9 controls the phenotypic switching in SCs by activation of the extracellular-signal-regulated kinase (ERK)1/2 via the neuregulin/ErbB and insulin growth factor (IGF)-1 ligand/receptor systems. As a result MMP-9 suppresses 5-bromo-2-deoxyuridine (BrdU) incorporation in cultured primary SC and the injured nerves.

MMP's such as MMP-9 are relatively well-characterized (see e.g. MMP-9 UNIPROT listing) and those of ordinary skill in the art can employ well-known techniques to identify "peptides having an affinity for said metalloproteinase (MMP) enzyme". The paper group from the paper by Turk have identified 6 different MMP peptides. See. e.g. Xu, et al., http://www.biochemj.org/bj/imps_x/pdf/BJ20050650.pdf. The following peptide ligands are from [Turk 2001], however the 'C' is the cysteine residue (thiol containing molecule) used to link the peptide to the QD surface. Also, the 'X' in MTI-MMP means that there is no preferred selectivity for that position in the peptide. The three dashes (---) is the bond that is cleaved (the scissile bond). The six peptides are presented hereinbelow. They may be used in various aspects of the invention either alone or in combination. Other peptides, as described above, may also be used in the present invention, including those peptides which are identified pursuant to certain methods as described herein.

```
MMP-7 substrate (matrilysin):
                             (SEQ ID NO: 1)
P-V-P-L-S---L-V-M-(C)
PVPLSLVMC MMP-1 substrate (Collagenase-1):
                             (SEQ ID NO: 2)
V-V-P-M-S---M-M-A-(C)
VVPMSMMAC MMP-2 substrate (Gelatinase A):
                             (SEQ ID NO: 3)
D-I-P-V-S---L-R-S-(C)
DIPVSLRSC MMP-9 substrate (Gelatinase B):
                             (SEQ ID No: 4)
V-V-P-L-S---L-R-S-(C)
VVPLSLRSC MMP-3 substrate (Stromelysin-1):
                             (SEQ ID NO: 5)
N-K-P-F-S---M-M-M-(C)
NKPFSMMMC MTI-MMP substrate (MMP-14):
                             (SEQ ID NO: 6)
F-I-P-X-S---L-R-M-(C)
FIPXSLRMC
```

"Evaluation of metalloproteinase (MMP) enzyme activity at pain signaling sites in the central nervous system (CNS) in real time" can include an assessment over a period of around 10, 9, 8, 7, 6, 5, 4, 3, 2, or 1 days, or around 48-36, or around 36-24, or around 24-12, or around 12-6, or around 6-1 hours, or around 60-45, or 45-30, or 30-15, or less than 15 minutes after a subject presents for diagnosis or begins treatment.

As used herein, the terms "peptide" or "polypeptide" refers broadly to a polymer of two or more amino acids joined together by peptide bonds. The term "polypeptide" also includes molecules which contain more than one polypeptide joined by a disulfide bond, or complexes of polypeptides that are joined together, covalently or noncovalently, as multimers (e.g., dimers, tetramers). Thus, the terms peptide, oligopeptide, and protein are all included within the definition of polypeptide and these terms are used interchangeably. It should be understood that these terms do not connote a specific length of a polymer of amino acids, nor are they intended to imply or distinguish whether the polypeptide is produced using recombinant techniques, chemical or enzymatic synthesis, or is naturally occurring.

Peptide and polypeptide sequences used in the invention also can be generated by phage display. A randomnized peptide or protein can be expressed on the surface of a phagemid particle as a fusion with a phage coat protein. Techniques of monovalent phage display are widely available (see, e.g., Lowman H. B. et al. (1991) Biochemistry 30:10832-8.) Phage expressing randomized peptide or protein libraries can be panned with a solid matrix to which a AAAA molecule has been attached. Remaining phage do not bind AAAA, or bind AAAA with substantially reduced affinity. The phage are then panned against a solid matrix to which a FRIP-1 has been attached. Bound phages are isolated and separated from the solid matrix by either a change in solution conditions or, for a suitably designed construct, by proteolytic cleavage of a linker region connecting the phage coat protein with the randomized peptide or protein library. The isolated phage can be sequenced to determine the identity of the selected antagonist.

Where necessary, standard techniques for growing cells, separating cells, and where relevant, cloning, DNA isolation, amplification and purification, for enzymatic reactions involving DNA ligase, DNA polymerase, restriction endonucleases and the like, and various separation techniques and protein syntheses are those known and commonly employed by those skilled in the art. A number of standard techniques are described in Sambrook et al., 1989 Molecular Cloning, Second Edition, Cold Spring Harbor Laboratory, Plainview, N.Y.; Maniatis et al., 1982 Molecular Cloning, Cold Spring Harbor Laboratory, Plainview, N.Y.; Wu (Ed.) 1993 Meth. Enzymol. 218, Part I; Wu (Ed.) 1979 Meth. Enzymol. 68; Wu et al., (Eds.) 1983 Meth. Enzymol. 100 and 101; Grossman and Moldave (Eds.) 1980 Meth. Enzymol. 65; Miller (ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setlow and Hollaender 1979 Genetic Engineering: Principles and Methods, Vols. 1-4, Plenum Press, New York. Abbreviations and nomenclature, where employed, are deemed standard in the field and commonly used in professional journals such as those cited herein.

High-content imaging techniques and diagnostic methods described herein can use fluorescence-inducing compounds, e.g. a fluorescent moiety such as a fluorescein dye or a rhodamine dye. In some embodiments, the fluorescent moiety comprises two or more fluorescent dyes that can act cooperatively with one another, for example by fluorescence resonance energy transfer ("FRET"). The fluorescent moiety may be any fluorophore that is capable of producing a detectable fluorescence signal in an assay medium; the fluorescence signal can be "self-quenched" and capable of fluorescing in an aqueous medium. "Quench" refers to a reduction in the fluorescence intensity of a fluorescent group as measured at a specified wavelength, regardless of the mechanism by which the reduction is achieved. As specific examples, the quenching may be due to molecular collision, energy transfer such as FRET, a change in the fluorescence spectrum (color) of the fluorescent group or any other mechanism. The amount of the reduction is not critical and may vary over a broad range. The only requirement is that the reduction be measurable by the detection system being used. Thus, a fluorescence signal is "quenched" if its intensity at a specified wavelength is reduced by any measurable amount.

Examples of fluorophores include xanthenes such as fluoresceins, rhodamines and rhodols, cyanines, phtalocyanines, squairanines, bodipy dyes, pyrene, anthracene, naphthalene, acridine, stilbene, indole or benzindole, oxazole or benzoxazole, thiazole or benzothiazole, carbocyanine, carbostyryl, prophyrin, salicylate, anthranilate, azulene, perylene, pyridine, quinoline, borapolyazaindacene, xanthene, oxazine or benzoxazine, carbazine, phenalenone, coumarin, benzofuran, or benzphenalenone. Examples of rhodamine dyes include, but are not limited to, rhodamine B, 5-carboxyrhodamine, rhodamine X (ROX), 4,7-dichlororhodamine X (dROX), rhodamine 6G (R6G), 4,7-dichlororhodamine 6G, rhodamine 110 (R110), 4,7-dichlororhodamine 110 (dR110), tetramethyl rhodamine (TAMRA) and 4,7-dichlorotetramethylrhodamine (dTAMRA). Examples of fluorescein dyes include, but are not limited to, 4,7-dichlorofluoresceins, 5-carboxyfluorescein (5-FAM) and 6-carboxyfluorescein (6-FAM).

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, for example Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2.sup.nd ed., 2001). See U.S. Pat. No. 6,420,108.

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Additionally, the present invention relates to embodiments that include methods for providing information over networks such as the Internet. For example, the components of the system may be interconnected via any suitable means including over a network, e.g. the ELISA plate reader to the processor or computing device. The processor may take the form of a portable processing device that may be carried by an individual user e.g. lap top, and data can be transmitted to or received from any device, such as for example, server, laptop, desktop, PDA, cell phone capable of receiving data, BLACKBERRY™, and the like. In some embodiments of the invention, the system and the processor may be integrated into a single unit. In another example, a wireless device can be used to receive information and forward it to another processor over a telecommunications network, for example, a text or multi-media message.

The functions of the processor need not be carried out on a single processing device. They may, instead be distributed among a plurality of processors, which may be interconnected over a network. Further, the information can be encoded using encryption methods, e.g. SSL, prior to transmitting over a network or remote user. The information required for decoding the captured encoded images taken from test objects may be stored in databases that are accessible to various users over the same or a different network.

In some embodiments, the data is saved to a data storage device and can be accessed through a web site. Authorized users can log onto the web site, upload scanned images, and immediately receive results on their browser. Results can also be stored in a database for future reviews.

In some embodiments, a web-based service may be implemented using standards for interface and data representation, such as SOAP and XML, to enable third parties to connect their information services and software to the data. This approach would enable seamless data request/response flow among diverse platforms and software applications.

In certain non-limiting embodiments, an increase or a decrease in a subject or test sample of the level of photon emission resulting from interaction of said metalloproteinase (MMP) enzyme and peptides having an affinity for said metalloproteinase (MMP) enzyme as compared to a comparable level of photon emission resulting from interaction of said metalloproteinase (MMP) enzyme and peptides having an affinity for said metalloproteinase (MMP) enzyme in a control subject or sample can be an increase or decrease in the magnitude of approximately ±5,000-10,000%, or approximately ±2,500-5,000%, or approximately ±1,000-2,500%, or approximately ±500-1,000%, or approximately ±250-500%, or approximately ±100-250%, or approximately ±50-100%, or approximately ±25-50%, or approximately ±10-25%, or approximately ±10-20%, or approximately ±10-15%, or approximately ±5-10%, or approximately ±1-5%, or approximately ±0.5-1%, or approximately ±0.1-0.5%, or approximately ±0.01-0.1%, or approximately ±0.001-0.01%, or approximately ±0.0001-0.001%.

The values obtained from controls are reference values representing a known health status and the values obtained from test samples or subjects are reference values representing a known disease status. The term "control", as used herein, can mean a sample of preferably the same source (e.g. blood, serum, tissue etc.) which is obtained from at least one healthy subject to be compared to the sample to be analyzed. In order to receive comparable results the control as well as the sample should be obtained, handled and treated in the same way. In certain examples, the number of healthy individuals used to obtain a control value may be at least one, preferably at least two, more preferably at least five, most preferably at least ten, in particular at least twenty. However, the values may also be obtained from at least one hundred, one thousand or ten thousand individuals.

Thus, in certain embodiments, the systems and methods of the invention utilize QD-based biosensing methods to detect spinal MMP activity in pain-signaling sites during peripheral neuropathy, discreetly identify MMP spinal cord enrichment at neuropathic pain-processing sites, identify and aid in the understanding of chronic neuroimmune neuropathies, can develop time resolved analyte activity calibration curves, provide a means for real time in vivo biosensing without releasing QDs into the biosensing environment, provide an in vivo method to monitor protease activity by inserting the QD biosensing probe through an in-dwelling catheter, monitor disease development and treatment evaluation, provide QD-based biosensing device with QDs consisting of duel fluorescent emissions that can be used in conjunction with one another to quantify and identify the analyte, can utilize the measurable change between two different fluorescent emissions occurring within the same QD upon excitation as a way to quantify analyte activity, can detect MMP activity from changes in QD fluorescence as a result of MMPs clipping peptides bioconjugated to QDs coupled to a substrate, and can quantify analyte activity from the measurable change in fluorescence due to FRET disruption between a QD donor and a QD acceptor as a result of analyte detection.

These and other aspects of the invention are illustrated further by the following non-limiting examples.

Example 1

Quantum Dot (QD) Modified Optical Fiber-Based Biosensor System

Figure 2:
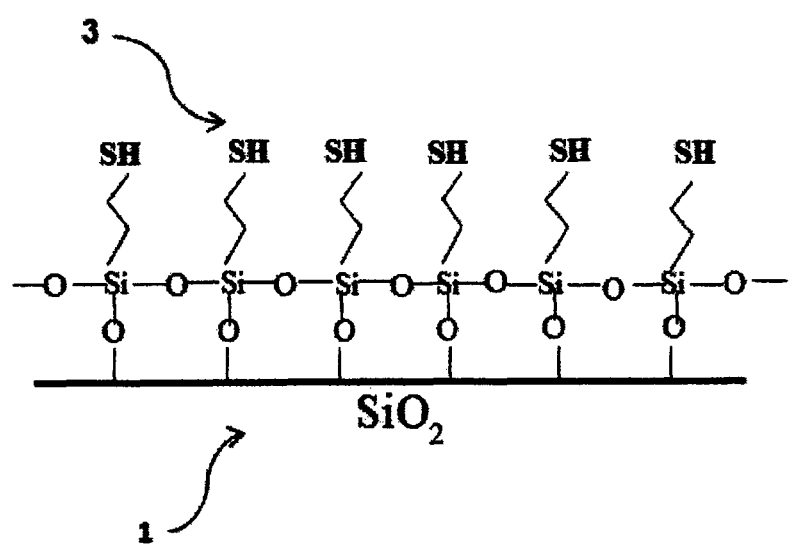
FIG. 2 is an illustration depicting mercaptopropyltrimethoxysilane (MPTMS) modified silica.
Figure 3:
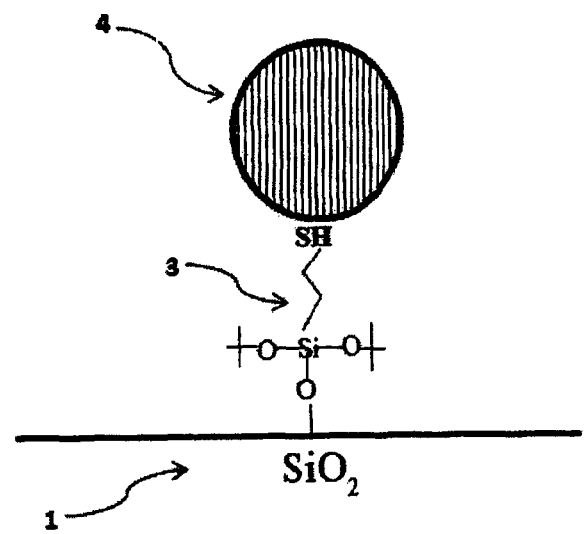
FIG. 3 is an illustration depicting a QD covalently bonded to silica by means of the MPTMS silane coupling agent.
Figure 4:
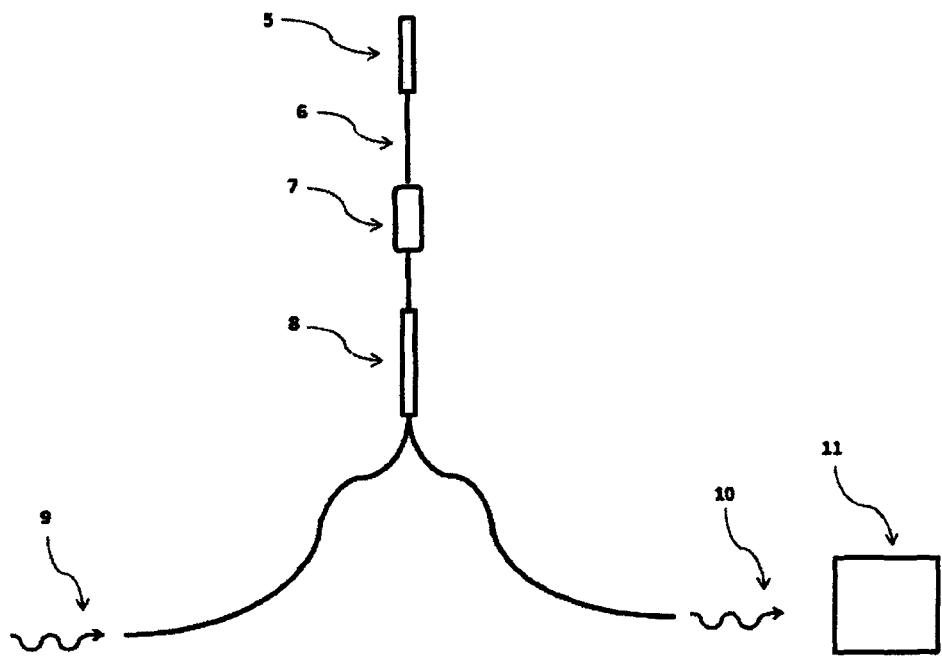
FIG. 4 is an illustration of the optical setup for performing QD modified optical fiber-based biosensing measurements for MMP activity, in vivo.

QDs are immobilized onto the silica surface of an optical fiber tip, via the use of the silane coupling agent, 3-mercaptopropyltrimethoxysilane (MPTMS), which contains a thiol functional group that covalently bonds to metallic surfaces, due to a known affinity between thiol molecules and metal. Hydrolyzable regions of MPTMS react with hydroxyl groups and form stable oxane bonds, and so a monolayer of the MPTMS silane coupling agent can be formed over hydroxyl modified silica [Hu 2001]. In FIG. 1, silica 1 is modified with hydroxyl groups 2, and in FIG. 2 MPTMS reacts with hydroxyl groups to form an MPTMS monolayer 3 with thiol molecules at the surface. In FIG. 3, Due to the aforementioned metal affinity from the thiol molecules, QDs 4 will be immobilized and covalently bonded to the thiol monolayer from the MPTMS. The optical setup in FIG. 4 for the biosensor will consist of a fiber optic laser setup with a PMT detector 11 and a Y-fiber (fiber coupler) 8 for duel entrance and exit of the excitation 9 and emission 10 lights, respectively. A fiber connector 7 is used to connect the QD tip-modified optical fiber 6 to the optical setup. The QD modified fiber is inserted through an in-dwelling catheter 5 in order to make MMP enzyme biosensing measurements in the intended medium.

Due to the highly sensitive surface properties of QDs, the optical properties of the photoluminescence can change upon surface modification. Changes in fluorescence emission can result when molecules are conjugated to the surface of QDs and further changes in fluorescence can occur when these conjugated molecules are modified. Similarly, bioconjugating peptides to the surface of QDs can affect the florescence emission of QDs, such as a change in the wavelength, and with MMP enzymes cleaving the bioconjugated peptides, an additional change in fluorescence can occur. It is the change in QD fluorescence properties that can occur from the MMPs cleaving peptides that is intended to be used and interpreted as a quantifiable analysis of MMP activity.

Figure 5:
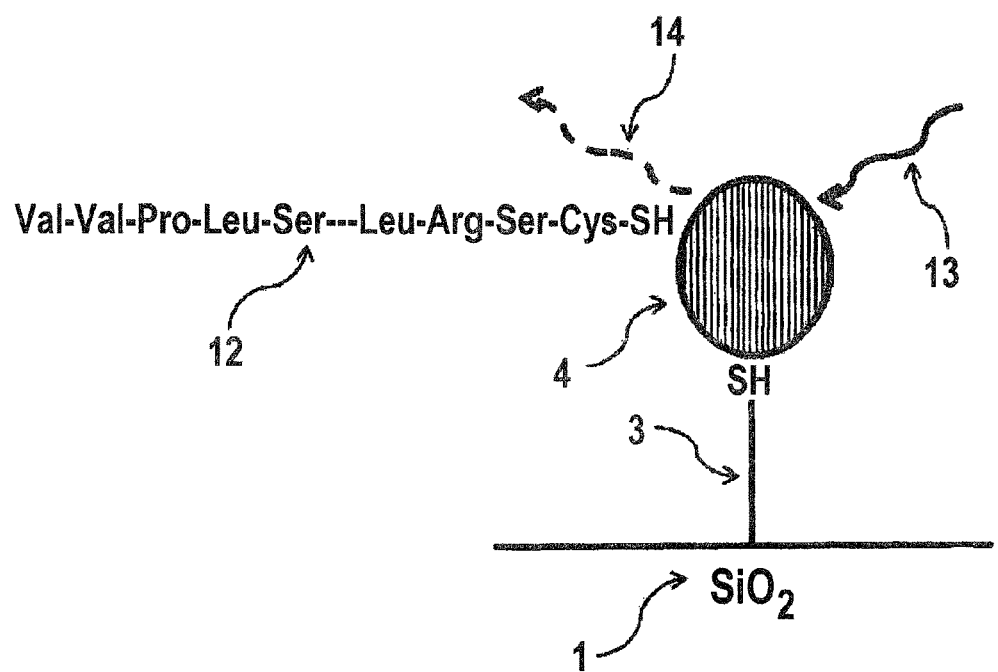
FIG. 5 is an illustration depicting a fluorescently excited QD covalently bonded to silica with a bioconjugated MMP substrate peptide at the surface.
Figure 6:
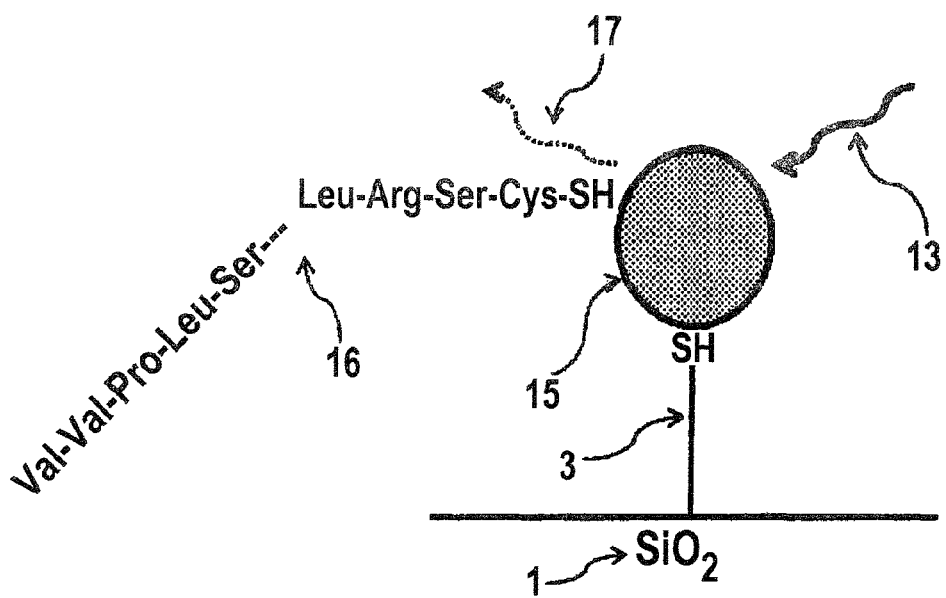
FIG. 6 is an illustration of a sensing method depicting the cleaved MMP substrate peptide resulting in altered QD fluorescence.

FIG. 5 and FIG. 6 illustrate changes in fluorescence as a result of active MMPs cleaving peptides. In FIG. 5, a QD 4 tethered to silica 1 from the MPTMS coupling agent 3 with the MMP peptide substrate 12 conjugated to its surface emits fluorescence 14 when excited by light 13 at a particular wavelength. In FIG. 6, the QD 15, illuminated by the same excitation light wavelength, undergoes a change in its optical properties and fluorescently emits light 17 at a different wavelength after the peptide 16 has been cleaved from an active MMP enzyme.

The effects that peptide conjugation has on the optical properties of doped non-cadmium containing QDs will be utilized as a means for MMP biosensing. Preliminary experiments involving synthesis and optical measurements of Mn-doped ZnSe/ZnS colloidal QDs have revealed a notable change in the photoluminescence properties between the synthesized QDs before and after applying a hydrophilic ZnS shell synthesis, suggesting surface sensitive effects to the QD emission.

Figure 7:
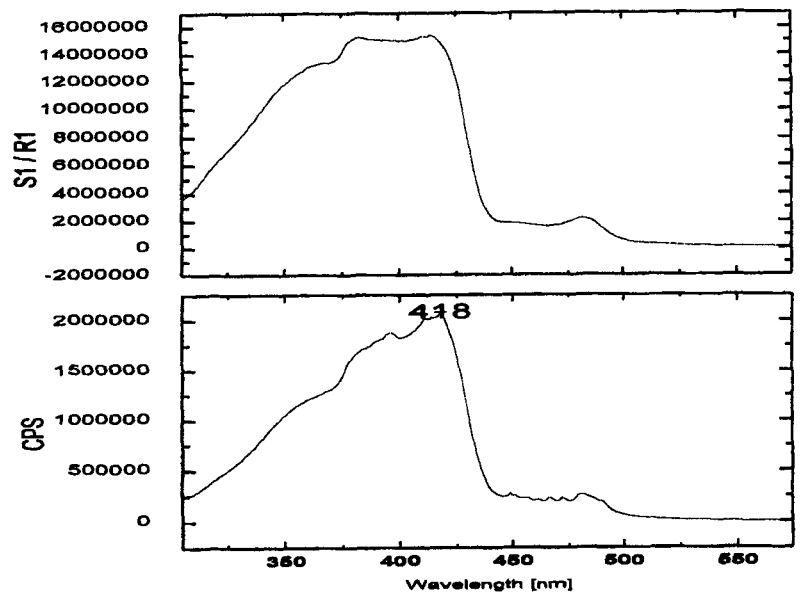
FIG. 7 is a normalized PL excitation spectrum and a raw PL excitation spectrum for atomic Mn transitions for hydrophobic Mn-doped ZnSe with ZnS shell QDs in toluene.
Figure 8:
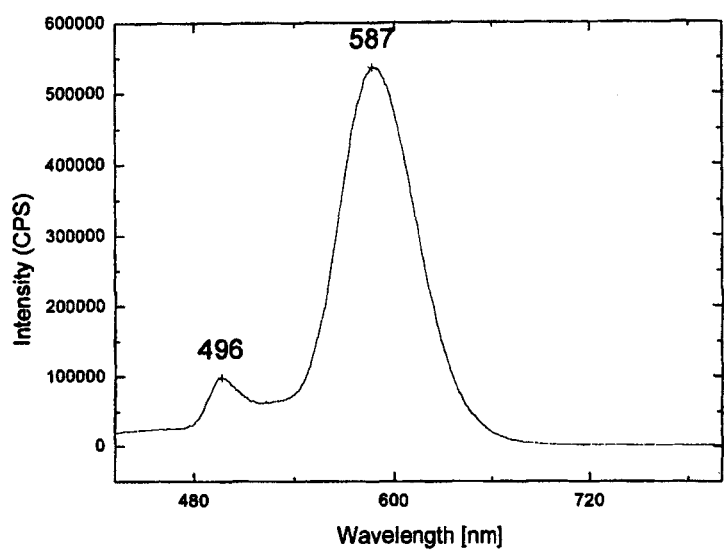
FIG. 8 is a PL emission spectrum for atomic Mn transitions for hydrophobic Mn-doped ZnSe with ZnS shell QDs in toluene.
Figure 9:
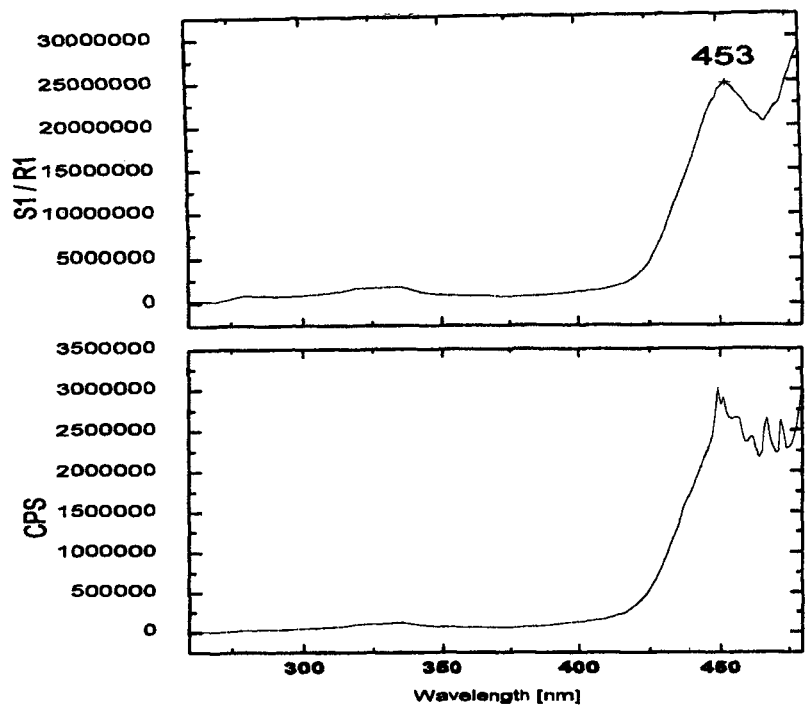
FIG. 9 is a normalized PL excitation spectrum and a raw PL excitation spectrum of ZnS defects for hydrophobic Mn-doped ZnSe with ZnS shell QDs in toluene.
Figure 10:
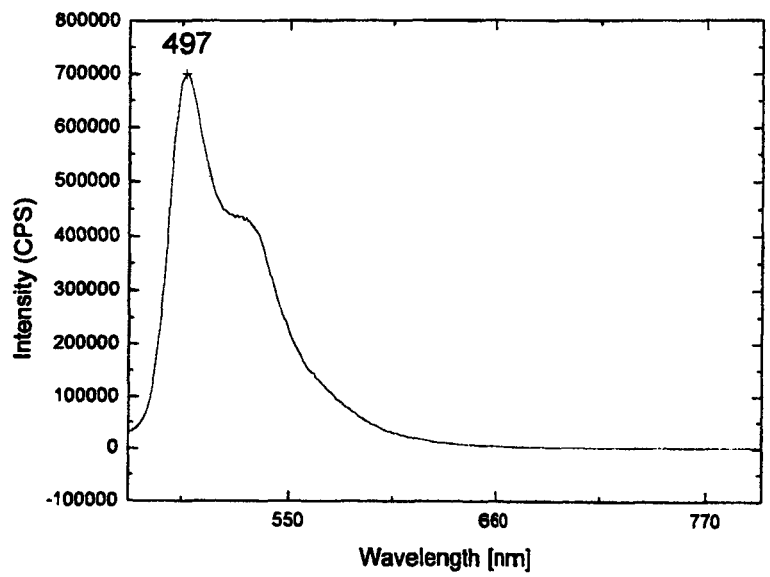
FIG. 10 is a PL emission spectrum of ZnS defects for hydrophobic Mn-doped ZnSe with ZnS shell QDs in toluene.

Mn-doped ZnSe/ZnS QDs were colloidally synthesized through modifications of a synthesis protocol by [Pradhan 2005] and [Acharya 2010], which were optically characterized with a spectrofluorometer. It was subsequently learned that the organically synthesized QDs exhibited 2 photoluminescence peaks, which emitted simultaneously two different emissions at a single excitation wavelength, with one emission being due to the dopant and the other being attributed to ZnS shell defects. FIG. 7 and FIG. 8 are the excitation and emission spectra for one of the transitions that take place, respectively, for Mn-doped ZnSe QDs in toluene. By using an excitation wavelength of 418 nm, two emission features show at 587 nm and 496 nm wavelengths. The 587 nm emission is believed to be from an atomic energy transition that takes place with Mn dopant and the 496 nm emission being from ZnS defects. By using 453 nm excitation wavelength the ZnS defect emission can be isolated. FIG. 9 and FIG. 10 are the excitation and emission spectra, respectively, for the ZnS defect transition that takes place for the Mn-doped ZnSe/ZnS QDs. Only the defect emission at the 497 nm wavelength, from the 453 nm excitation wavelength, can be observed in FIG. 10.

Figure 11:
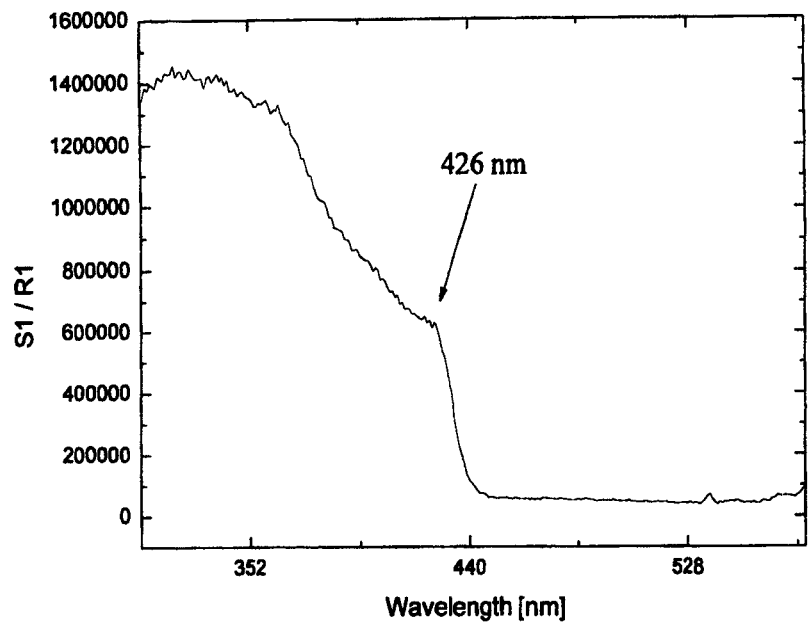
FIG. 11 is a normalized PL excitation spectrum for atomic Mn transitions for hydrophilic Mn-doped ZnSe with ZnS shell QDs in water.
Figure 12:
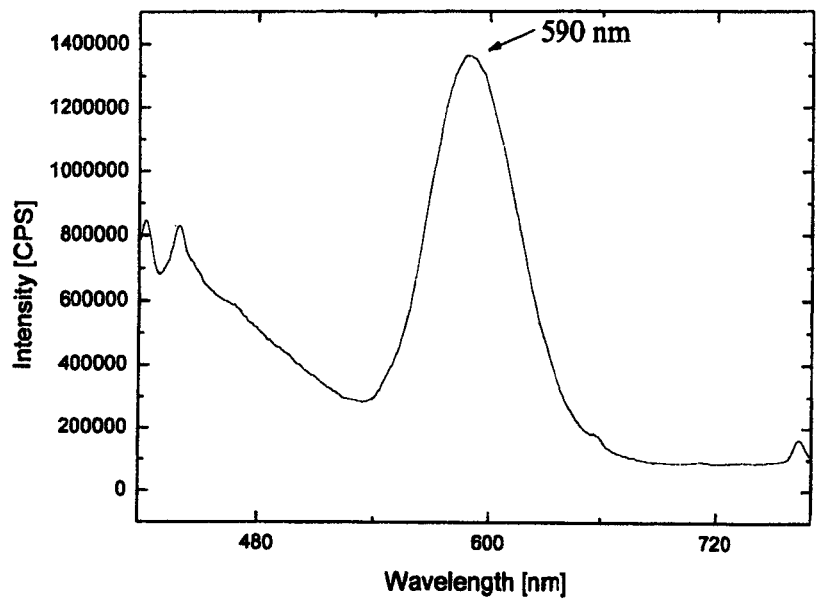
FIG. 12 is a PL emission spectrum for atomic Mn transitions for hydrophilic Mn-doped ZnSe with ZnS shell QDs in water.

Upon applying a hydrophilic ZnS shell synthesis, based off of a modification by [Li 2008] to the Mn-doped ZnSe QDs, in which QDs could be made dispersable in water due to charged carboxyl groups at the surface, the 497 nm emission line would no longer show, suggesting surface sensitivity to this particular transition. Consequently, The hydrophillic QDs would only exhibit an emission peak at 590 nm, and with a significant blue shift of the excitation wavelength. FIG. 11 and FIG. 12 show the excitation and emission spectra of the hydrophillic QDs, respectively, where only the 597 nm Mn emission can be observed. The hydrophilization involves a thiol containing molecule that attaches to the surface, and the result is that the 497 nm ZnS defect emission vanishes. Therefore, by attaching peptides to the QDs from a thiol based bond, the 497 ZnS defect emission will subsequently disappear, or weaken, and will be progressively recovered as a result of MMPs cleaving the peptides. The ratio of orange 587 nm emission to that of recovered 497 nm emission will be the basis for the optical transducer mechanism for measuring MMP activity with QDs.

Example 2

Förster Resonant Energy Transfer (FRET)

Figure 13:
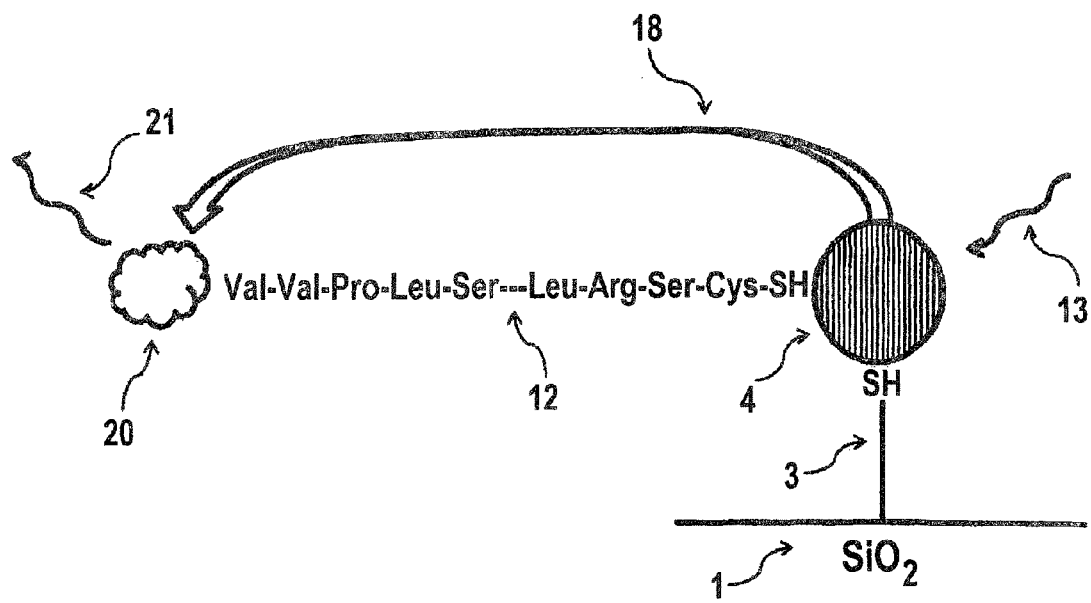
FIG. 13 is an illustration depicting Förster resonance energy transfer (FRET) between a QD donor tethered to silica and a fluorescent protein, or dye, acceptor.
Figure 14:
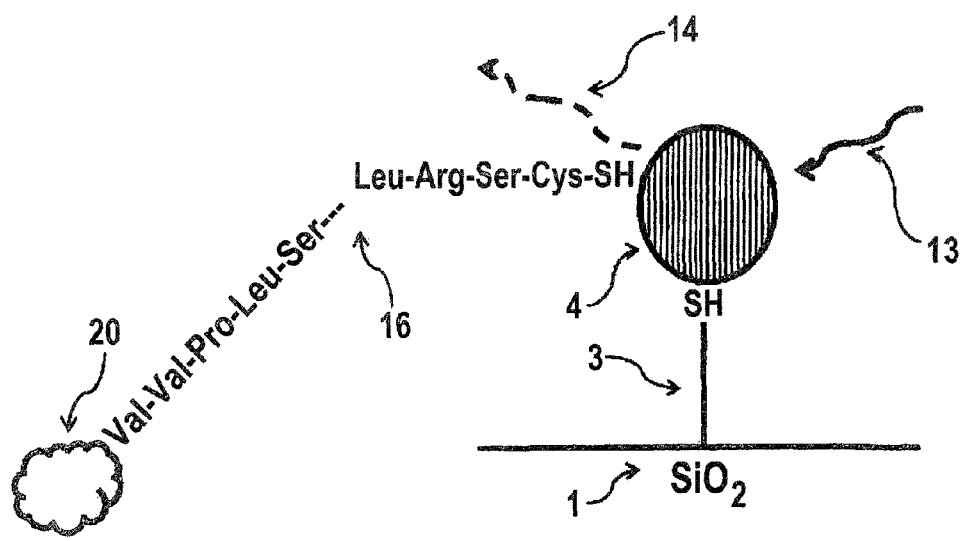
FIG. 14 is an illustration depicting FRET disruption between a QD donor tethered to silica and a fluorescent protein, or dye, acceptor.

QD-modified optical fiber based MMP biosensing in accordance with the invention may also emply Förster resonant energy transfer (FRET) between QD donors and fluorescent peptide, or dye, acceptors. The embodiment consists of QDs covalently linked to silica optical fiber tip surfaces with MMP substrate peptides, modified at either the N or C-terminals with fluorescent proteins or dyes, covalently linked to the QDs. A fluorescent protein with an absorption spectrum that overlaps the emission spectrum of the QD will result in FRET, when the 2 fluorophores are in close enough vicinity. This means that the protein will fluoresce due to an energy transfer that occurs from the QD emission while the 2 fluorophores are being illuminated with light at a wavelength that excites the QD only. In FIG. 13, light 13 that excites the QD 4 results in an energy transfer (FRET) 18 to a fluorescent protein, or dye, 20 that is linked to the QD surface, via the MMP peptide substrate 12, and fluorescence emission 21 from the protein results. As a sensing method, it is intended to utilize the FRET disruption that results from the cleaving of the peptide from the targeted MMP enzyme as a measurable parameter for enzyme activity. In FIG. 14, the peptide 16 is cleaved from the MMP enzyme, the fluorescent protein 20 falls out of range for FRET to occur and the fluorescence from the protein, or dye, 20 diminishes and is replaced by the QD fluorescence 14. In an ensemble of QDs with conjugated fluorescence proteins, the ratiometric change that occurs as QD fluorescence increases and protein fluorescence decreases, due to MMP activity, can be used as a reliable quantifiable method of measuring MMP activity under in vivo conditions.

Example 3

QD FRET Acceptors and Donors Attached with a Single Peptide

Figure 15:
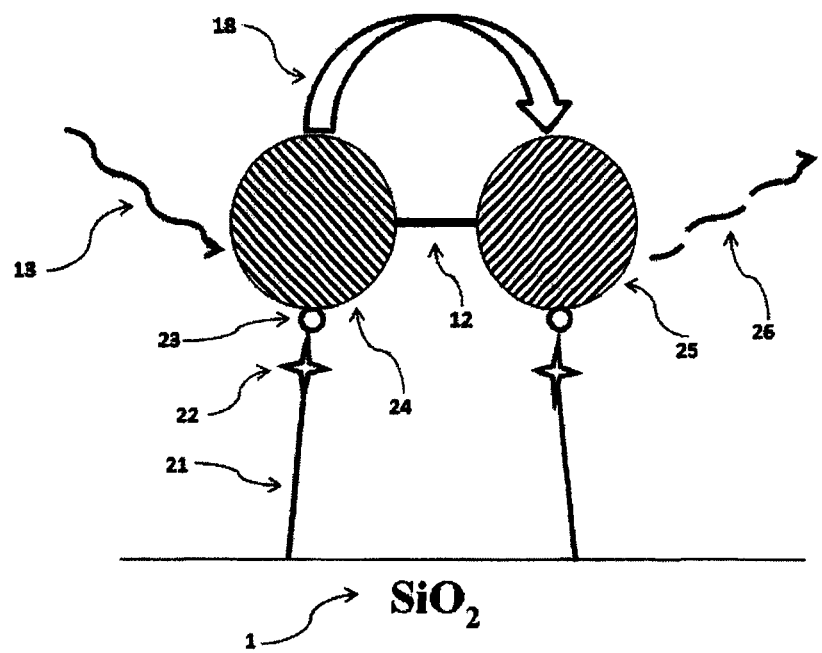
FIG. 15 is an illustration depicting FRET between a tethered QD donor and a tethered QD acceptor.
Figure 16:
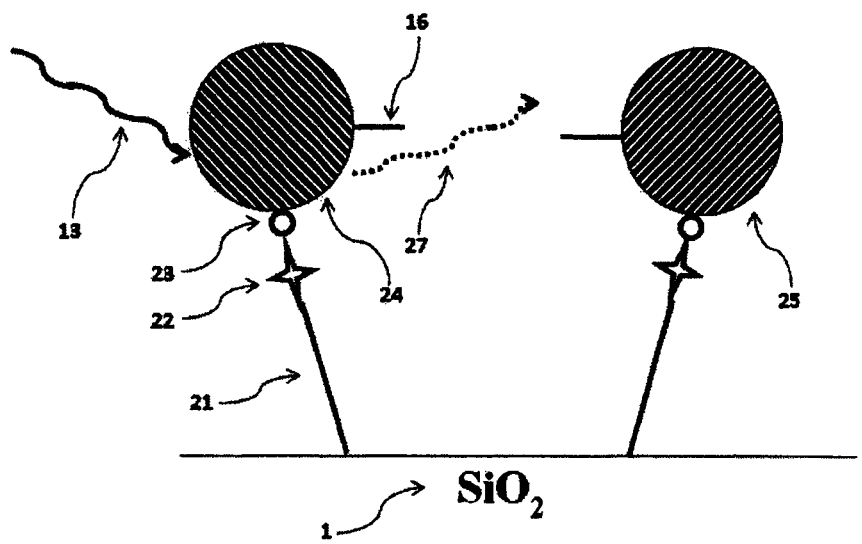
FIG. 16 is an illustration depicting FRET disruption between a tethered QD donor and a tethered QD acceptor.

A QD modified optical fiber-based MMP biosensor of the invention can also employ a QD FRET acceptors and donors attached with a single peptide, without the use of fluorescent peptides or dyes. The optical fiber modification involves tethering QD Forster Resonance Energy Transfer (FRET) pairs linked together with a peptide onto the tip of a multimode silica optical fiber, via a silane coupling agent. In FIG. 15, a peptide sequenced for the particular MMP of interest 12 is used to link a QD donor 13 and a QD acceptor 25, that are both tethered to silica 1, by means of the affinity interaction between biotin 23 and a streptavidin 22 modified silane coupling agent 21. The short distance between the QD donor and acceptor as a result of the peptide linker results in FRET 18 between the 2 QD fluorophores. The excitation light 13 transfers energy from the QD donor 24 to the QD acceptor 25 resulting in the fluorescence 26 of the acceptor. In FIG. 16, Quantitative ratio-metric data involving MMP activity can be recorded based on the FRET disruption, which results from active MMPs in the CSF clipping the peptide 16 molecules linking the illuminated QD pairs. The FRET disruption causes fluorescence 27 in the QD donor 24 and a decrease or elimination to the fluorescence in the QD acceptor 25. The degree of change between the intensity of the donor emission to that of the acceptor is used to characterize MMP activity.

Thermally excited electrons and lattice vibrations that result from heated QDs contribute to a significant loss in PL intensity and quantum efficiency. The intended application involves biosensing inside of the human body (~37° C.) from QD FRET pairs and the loss of PL intensity at the elevated body temperature is perceived as a potential problem. In order to maintain better thermal PL stability a synthesis by [Acharya 2010] and [Pradhan 2005] for green emitting doped ZnSe QD donors and a synthesis by [Xie 2009] for red emitting doped InP QD acceptors was modified in order to achieve QD luminescence with little loss at the elevated body temperature. The low PL loss may be due to the Cu impurity that is doped into the nanocrystal lattice which is due to atomic transitions that aren't as coupled to the lattice vibrations [Xie 2009].

Figure 17:
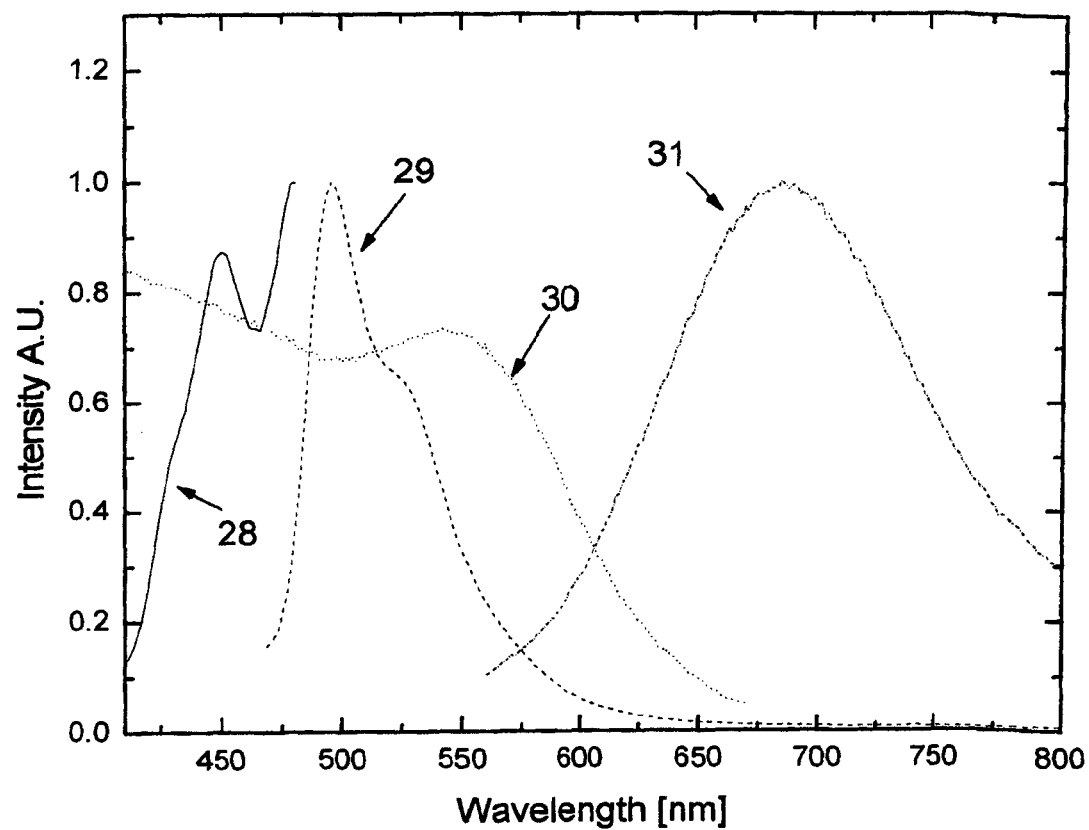
FIG. 17 is a PL spectrum depicting overlap between the emission spectrum of the Cu-doped ZnSe QD donor and the excitation spectrum of the Cu-doped InP/ZnSe QD acceptor.

The PL spectral data for Cu-doped ZnSe and InP/ZnSe QDs have sufficient spectral overlap for FRET to occur between the donor and acceptor QDs. In FIG. 17, the emission spectrum 29 of the Cu-doped ZnSe donor overlaps the excitation spectrum 30 of the Cu-doped InP QD acceptor. The excitation spectrum of the donor 28 overlaps the excitation spectrum 30 of the acceptor, and the emission spectrum of the donor 29 and the emission spectrum of the acceptor 31 are well separated and the ratiometric change between the emission intensities of the donor and acceptor is the parameter used to quantify MMP activity, in vivo.

REFERENCES

[Acharya 2010] Acharya S, Sarma D, Jana N and Pradhan N. "An Alternate Route to High-Quality ZnSe and Cu-Doped ZnSe Nanocrystals." J. Phys. Chem. Lett. 2010, 1, 485-488.

[Adair 2004] Adair J, Charlie J, Dencoff J, Kaye J, Quinn J, Camicioli R, Stetler-Stevenson W, Rosenberg G "Measurement of gelatinase B in the cerebrospinal fluid of patients with vascular dementia and Alzheimer disease", Stroke 2004: 35:e159-e162.

[Dev 2010] Dev R, Srivastava P K, Iyer J P, Dastidar S G, Ray A, "Therapeutic potential of matrix metalloprotease inhibitors in neuropathic pain", Expert Opinion on Investigational Drugs April 2010, Vol. 19, No. 4: 455-468

[Hu 2001] Hu M., Noda S., Okubo T., Yamaguchi Y., Komiyama H. "Structure and morphology of self-assembled 3-mercaptopropyltrimethoxysilane layers on silicon oxide", Applied Surface Science 181 (2001) 307-316.

[Leppert 1998] Leppert D, Ford J, Stabler G S Grygar C, Lienert C, Huber S, Miller H, Hauser S, Kappos L, "Matrix metalloproteinase-9 is selectively elevated in CSF during relapses and stable phases of multiple sclerosis", Brain (1998), 121, 2327-2334.

[Li 2008] Li C, Ando M, Enomoto H, and Murase N, "Highly luminescent water-soluble InP/ZnS nanocrystals prepared via reactive phase transfer and photochemical processing", J. Phys. Chem. C 2008, 112, 20190-20199.

[Liuzzi 2000] Liuzzi G M, Mastroianni C M, Santacroce M P, Fanelli M, D'agostino C, Vullo V, Riccio P, "Increased activity of matrix metalloproteinases in the cerebrospinal fluid of patients with HIV-associated neurological diseases", Journal of Neurovirology 2000, 6: 156-163.

[Melville 2011] Melville P, Benites N, Ruz-Perez M, Yokoya E, "Proteinase and phospholipase activities and development at different temperatures of yeasts of yeasts isolated from bovine milk", Journal of Dairy Research, 2011, 78, 385-390.

[Niebroj-Dobosz 2010] Niebroj-Dobosz I, Janik P, Sokolowska B, and Kwiecinski H, "Matrix metalloproteinases and their tissue inhibitors in serum and cerebrospinal fluid of patients with amyotrophic lateral sclerosis", European Journal of Neurology 2010, 17: 226-231.

[Pradhan 2005] Pradhan N, Goorskey D, Thessing J, and Peng X, "An Alternative of CdSeNanocrystal Emitters: Pure and Tunable Impurity Emissions in ZnSeNanocrystals." J. Am. Chem. Soc. 2005, 127(50), 17586-17587.

[Turk 2001] Turk B, Huang L, Piro E, Cantley L, "Determination of protease cleavage site motifs using mixture-based oriented peptide libraries", Nature Biotechnology, July 2001, 19: 661-667

[Wagner 2009] Wagner K, "The need for biomarkers in amyotrophic lateral sclerosis development", Neurology 2009; 72: 11-12.

[Xie 2009] Xie, R G.: Peng, X G, Synthesis of Cu-doped InP Nanocrystals (d-dots) with ZnSe Diffusion Barrior as Efficient and Color-Tunable NIR emitters", J. Am. Chem. Soc. 2009, 131, 30, 10645-10651

What is claimed is:

1. A quantum dot (QD) modified optical fiber-based biosensor system adapted for evaluation of metalloproteinase (MMP) enzyme activity at pain signaling sites in the central nervous system (CNS), said biosensor system comprising:
   a multimode silica optical fiber comprising one or more quantum dots that are bioconjugated on their surface to one or more peptides having an affinity for said metalloproteinase (MMP) enzyme, and that are tethered to an insertion end of said multimode silica optical fiber by one or more silane coupling agents; and
   a photon detector;
   wherein changes in photon emission resulting from interaction of said metalloproteinase (MMP) enzyme and peptides having an affinity for said metalloproteinase (MMP) enzyme are detected by said photon detector, said multimode silica optical fiber is tethered to a quantum dot donor and to a quantum dot acceptor by one or more biotin and streptavidin-modified silane coupling agents; and
   said quantum dot donor and quantum dot acceptor are linked by a peptide having an affinity for said metalloproteinase (MMP) enzyme.

2. A method for evaluating in vivo metalloproteinase (MMP) enzyme activity at a subject's central nervous system pain signaling site, the method comprising:
   a) providing a quantum dot (QD) modified optical fiber-based biosensor system adapted for evaluation of metalloproteinase (MMP) enzyme activity at pain signaling sites in the central nervous system (CNS), said biosensor system comprising:
      a multimode silica optical fiber comprising one or more quantum dots that (1) are bioconjugated on their surface to one or more peptides having an affinity for said metalloproteinase (MMP) enzyme, and (2) that are tethered to an insertion end of said multimode silica optical fiber by one or more silane coupling agents; and
      a photon detector;
      wherein changes in photon emission resulting from interaction of said metalloproteinase (MMP) enzyme and peptides having an affinity for said metalloproteinase (MMP) enzyme are detected by said photon detector, the one or more peptides having an affinity for said metalloproteinase (MMP) enzyme are modified at either their N or C-terminals with a fluorescent protein or dye,
      in operation, the fluorescent protein or dye undergoes Förster resonant energy transfer (FRET) with the quantum dots, said Förster resonant energy transfer (FRET) being disrupted by interaction of said metalloproteinase (MMP) enzyme and peptides having an affinity for said metalloproteinase (MMP) enzyme; and wherein said disruption is detected by said photon detector, and correlated as an indicator of metalloproteinase (MMP) enzyme activity;
   b) inserting the multimode silica optical fiber of the said biosensor system into an in-dwelling spinal catheter that is submerged into either the epidermal or intrathecal regions of the subject's central nervous system; and
   c) measuring changes in Förster resonant energy transfer (FRET) disruption caused by interaction of said metalloproteinase (MMP) enzyme and peptides having an affinity for said metalloproteinase (MMP) enzyme, said changes having been detected by said photon detector.

3. The method according to claim 2 wherein the method is conducted in high-throughput format and in real-time.

4. A method for evaluating in vivo metalloproteinase (MMP) enzyme activity at a subject's central nervous system pain signaling site, the method comprising:
   a) providing a quantum dot (QD) modified optical fiber-based biosensor system adapted for evaluation of metalloproteinase (MMP) enzyme activity at pain signaling sites in the central nervous system (CNS), said biosensor system comprising:
      a multimode silica optical fiber comprising one or more quantum dots that (1) are bioconjugated on their surface to one or more peptides having an affinity for said metalloproteinase (MMP) enzyme, and (2) that are tethered to an insertion end of said multimode silica optical fiber by one or more silane coupling agents; and
      a photon detector;
      wherein changes in photon emission resulting from interaction of said metalloproteinase (MMP) enzyme and peptides having an affinity for said metalloproteinase (MMP) enzyme are detected by said photon detector,
      the one or more peptides having an affinity for said metalloproteinase (MMP) enzyme are modified at either their N or C-terminals with a fluorescent protein or dye which undergoes Förster resonant energy transfer (FRET) with the quantum dots, said Förster resonant energy transfer (FRET) being disrupted by interaction of said metalloproteinase (MMP) enzyme and peptides having an affinity for said metalloproteinase (MMP) enzyme;
      wherein said disruption is detected by said photon detector, and correlated as an indicator of metalloproteinase (MMP) enzyme activity, the photon detector being adapted for the detection of ratiometric changes that occur as quantum dot fluorescence increases and protein fluorescence decreases due to metalloproteinase (MMP) enzyme activity, and wherein in operation said detected ratiometric changes are correlated as an indicator of metalloproteinase (MMP) enzyme activity in vivo b) inserting the multimode silica optical fiber of the said biosensor system into an in-dwelling spinal catheter that is submerged into either the epidermal or intrathecal regions of the subject's central nervous system; and c) measuring ratiometric changes that occur as quantum dot fluorescence increases and protein fluorescence decreases due to metalloproteinase (MMP) enzyme activity, said changes having been detected by said photon detector.

5. The method according to claim 4 wherein the method is conducted in high-throughput format and in real-time.

6. A method for identifying a peptide having an affinity for a metalloproteinase (MMP) enzyme implicated in a neuroimmune neuropathy, the method comprising:

a) providing a quantum dot (QD) modified optical fiber-based biosensor system adapted for evaluation of metalloproteinase (MMP) enzyme activity at pain signaling sites in the central nervous system (CNS), said biosensor system comprising:

a multimode silica optical fiber adapted for insertion into an in-dwelling spinal catheter that is submerged into either the epidermal or intrathecal regions of the central nervous system of a subject comprising one or more quantum dots that are bioconjugated on their surface to one or more peptides having an affinity for said metalloproteinase (MMP) enzyme, and that are tethered to an insertion end of said multimode silica optical fiber by one or more silane coupling agents; and a photon detector;

wherein changes in photon emission resulting from interaction of said metalloproteinase (MMP) enzyme and peptides having an affinity for said metalloproteinase (MMP) enzyme are detected by said photon detector and the one or more peptides having an affinity for said metalloproteinase (MMP) enzyme are modified at either their N or C-terminals with a fluorescent protein or dye, in operation, the fluorescent protein or dye undergoes Förster resonant energy transfer (FRET) with the quantum dots, said Förster resonant energy transfer (FRET) being disrupted by interaction of said metalloproteinase (MMP) enzyme and peptides having an affinity for said metalloproteinase (MMP) enzyme, said disruption being (1) detected by said photon detector, and (2) correlated as an indicator of metalloproteinase (MMP) enzyme activity, wherein said photon detector is adapted for the detection of ratiometric changes that occur as quantum dot fluorescence increases and protein fluorescence decreases due to metalloproteinase (MMP) enzyme activity, and wherein in operation said detected ratiometric changes are correlated as an indicator of metalloproteinase (MMP) enzyme activity in vivo;

b) inserting said multimode silica optical fiber of said biosensor system into said in-dwelling spinal catheter;

c) measuring any ratiometric changes that occur as a result of quantum dot fluorescence increases and protein fluorescence decreases due to metalloproteinase (MMP) enzyme activity, as detected by said photon detector; and d) comparing any changes in photon emission to a control value.

7. The method according to claim 6 wherein said silane coupling agents comprise a thiol functioning group that covalently bonds to a metallic surface.

8. The method according to claim 7 wherein said silane coupling agent is 3-mercaptopropyltrimethoxysilane (MPTMS).

9. The method according to claim 6 wherein said biosensor contains a fiber optic laser comprising a PMT detector and a Y-fiber fiber coupler adapted for duel entrance and exit of excitation and emission lights, respectively and a fiber connector is connected to the insertion end of said multimode silica optical fiber.

10. The method according to claim 6 wherein the method is conducted in high-throughput format and in real-time.

* * * * *

```
                          SEQUENCE LISTING

<160> NUMBER OF SEQ ID NOS: 6

<210> SEQ ID NO 1
<211> LENGTH: 9
<212> TYPE: PRT
<213> ORGANISM: Homo sapiens

<400> SEQUENCE: 1

Pro Val Pro Leu Ser Leu Val Met Cys
1               5

<210> SEQ ID NO 2
<211> LENGTH: 9
<212> TYPE: PRT
<213> ORGANISM: Homo sapiens
<220> FEATURE:
<221> NAME/KEY: misc_feature
<223> OTHER INFORMATION: MMP-1 substrate (Collagenase-1)

<400> SEQUENCE: 2

Val Val Pro Met Ser Met Met Ala Cys
1               5

<210> SEQ ID NO 3
<211> LENGTH: 9
<212> TYPE: PRT
<213> ORGANISM: Homo sapiens
<220> FEATURE:
<221> NAME/KEY: misc_feature
<223> OTHER INFORMATION: MMP-2 substrate (Gelatinase A)

<400> SEQUENCE: 3

Asp Ile Pro Val Ser Leu Arg Ser Cys
1               5

<210> SEQ ID NO 4
<211> LENGTH: 9
<212> TYPE: PRT
<213> ORGANISM: Homo sapiens
<220> FEATURE:
<221> NAME/KEY: misc_feature
<223> OTHER INFORMATION: MMP-9 substrate (Gelatinase B)

<400> SEQUENCE: 4

Val Val Pro Leu Ser Leu Arg Ser Cys
1               5

<210> SEQ ID NO 5
<211> LENGTH: 9
<212> TYPE: PRT
<213> ORGANISM: Homo sapiens
<220> FEATURE:
<221> NAME/KEY: misc_feature
<223> OTHER INFORMATION: MMP-3 substrate (Stromelysin-1)

<400> SEQUENCE: 5

Asn Lys Pro Phe Ser Met Met Met Cys
1               5

<210> SEQ ID NO 6
<211> LENGTH: 9
<212> TYPE: PRT
<213> ORGANISM: Homo sapiens
<220> FEATURE:
<221> NAME/KEY: misc_feature
```

```
<223> OTHER INFORMATION: MTI-MMP substrate (MMP-14)
      X means that there is no preferred selectivity for that position
      in the peptide.
<220> FEATURE:
<221> NAME/KEY: misc_feature
<222> LOCATION: (4)..(4)
<223> OTHER INFORMATION: Xaa can be any naturally occurring amino acid

<400> SEQUENCE: 6

Phe Ile Pro Xaa Ser Leu Arg Met Cys
1               5
```